United States Patent [19]

Knotek

[11] Patent Number: 5,531,704

[45] Date of Patent: Jul. 2, 1996

[54] NEEDLE PUNCTURE PREVENTION DEVICE

[75] Inventor: Evan M. Knotek, Wilmington, N.C.

[73] Assignee: EMK Enterprises, LLC, Wilmington, N.C.

[21] Appl. No.: 398,300

[22] Filed: Mar. 3, 1995

[51] Int. Cl.$^6$ ...................................... A61M 5/32
[52] U.S. Cl. ........................... 604/192; 604/198; 604/263; 604/110; 128/919
[58] Field of Search .................................... 604/263, 163, 604/110, 187, 192, 198, 905; 128/919

[56] References Cited

U.S. PATENT DOCUMENTS

| | | |
|---|---|---|
| 4,725,267 | 2/1988 | Vaillancourt . |
| 4,735,618 | 4/1988 | Hagen ..................................... 604/192 |
| 4,747,835 | 5/1988 | Sandhaus . |
| 4,790,828 | 12/1988 | Dombrowski et al. .................. 604/198 |
| 4,850,968 | 7/1989 | Romano . |
| 4,898,589 | 2/1990 | Dolgin et al. ........................... 604/198 |
| 4,935,013 | 6/1990 | Haber et al. ............................. 604/263 |
| 4,950,250 | 8/1990 | Haber et al. ............................. 604/192 |
| 4,998,922 | 3/1991 | Kuracina et al. ........................ 604/263 |
| 5,066,279 | 11/1991 | Russell . |
| 5,137,521 | 8/1992 | Wilkins . |
| 5,163,907 | 11/1992 | Szuszkiewicz . |
| 5,215,534 | 6/1993 | De Harde et al. . |
| 5,267,972 | 12/1993 | Anderson . |
| 5,295,972 | 3/1994 | Mischenko .............................. 604/263 |
| 5,295,974 | 3/1994 | O'Laughlin . |
| 5,295,975 | 3/1994 | Lockwood, Jr. . |
| 5,312,369 | 5/1994 | Arcusin et al. . |
| 5,314,503 | 5/1994 | Bobrove et al. . |
| 5,322,517 | 6/1994 | Sircom et al. . |
| 5,334,158 | 8/1994 | McLees . |
| 5,342,308 | 8/1994 | Boschetti . |
| 5,342,309 | 8/1994 | Hausser . |
| 5,342,310 | 8/1994 | Ueyama et al. . |
| 5,356,395 | 10/1994 | Chen . |
| 5,364,359 | 10/1994 | Van Den Haak . |
| 5,364,360 | 11/1994 | Flumene et al. . |
| 5,364,370 | 11/1994 | Szerlip et al. . |
| 5,366,447 | 11/1994 | Gurley . |
| 5,368,568 | 11/1994 | Pitts et al. . |
| 5,368,577 | 11/1994 | Teoh et al. . |
| 5,370,619 | 12/1994 | Rossi . |
| 5,370,623 | 12/1994 | Kreamer . |
| 5,370,628 | 12/1994 | Allison et al. . |
| 5,372,590 | 12/1994 | Haber et al. . |
| 5,374,250 | 12/1994 | Dixon . |
| 5,374,255 | 12/1994 | Nathan et al. . |
| 5,376,080 | 12/1994 | Petrussa . |
| 5,385,550 | 1/1995 | Su et al. . |
| 5,385,555 | 1/1995 | Hausser . |
| 5,385,557 | 1/1995 | Thompson . |

OTHER PUBLICATIONS

1991 Modern Healthcare, Jan. 14, 1991.
Machine Design, Sep. 12, 1994.
New Orleans City Business, Mar, 14, 1994.
Plastics World, Aug. 1993.
The Hartford Courant, Sep. 13, 1994.

Primary Examiner—John D. Yasko
Assistant Examiner—Ronald K. Stright, Jr.
Attorney, Agent, or Firm—Jones, Day, Reavis & Pogue

[57] ABSTRACT

A device for preventing accidental needle puncture injuries comprises a sleeve for attachment to a needle or a needle and syringe assembly prior to use. The sleeve has a relaxed condition in which the needle is passed through an eccentrically positioned opening in a top member and exposed for use. The needle hub and/or syringe is firmly anchored by a base member. The top and base members are interconnected by living hinges to a pair of oppositely inverted sidewalls each comprising two members of unequal length interconnected by sidewall living hinges which are open when the device is in a relaxed condition. After needle use, the sidewalls are manually biased toward each other by the user, thereby closing the sidewall hinges, and the device assumes an extended condition. The needle is thereby extracted from the top member opening and the needle tip is engaged by top member needle tip engaging configuration. Elements are also provided for trapping the needle in the device after use.

22 Claims, 8 Drawing Sheets

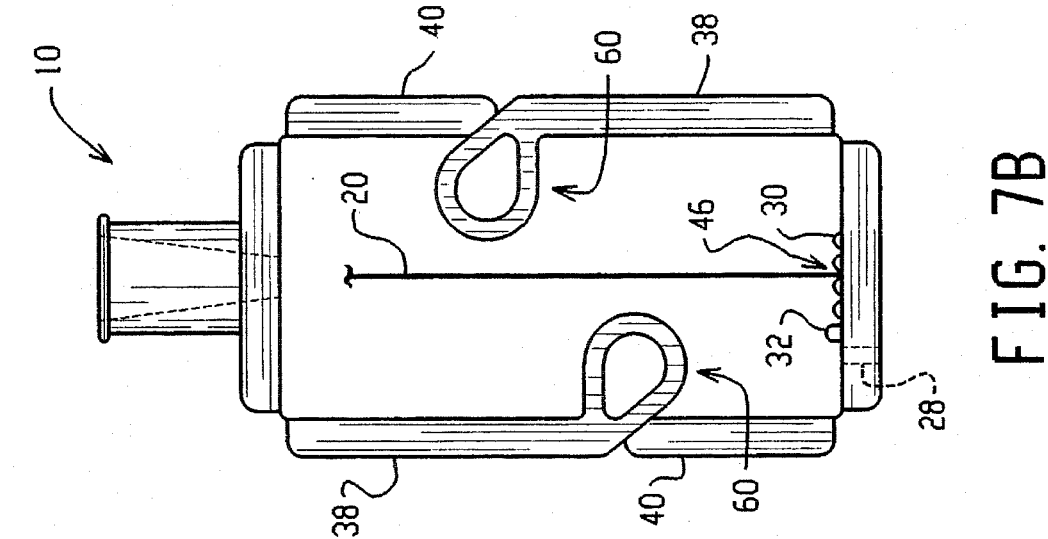
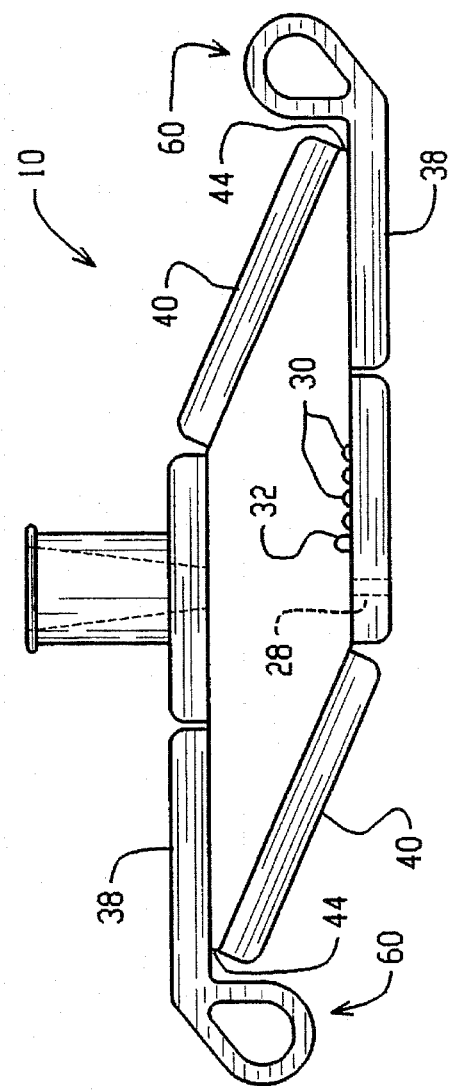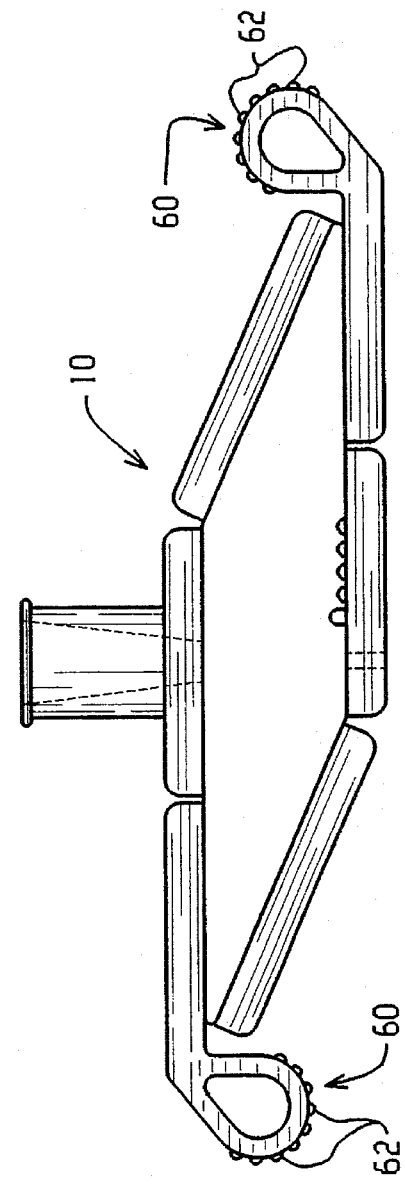

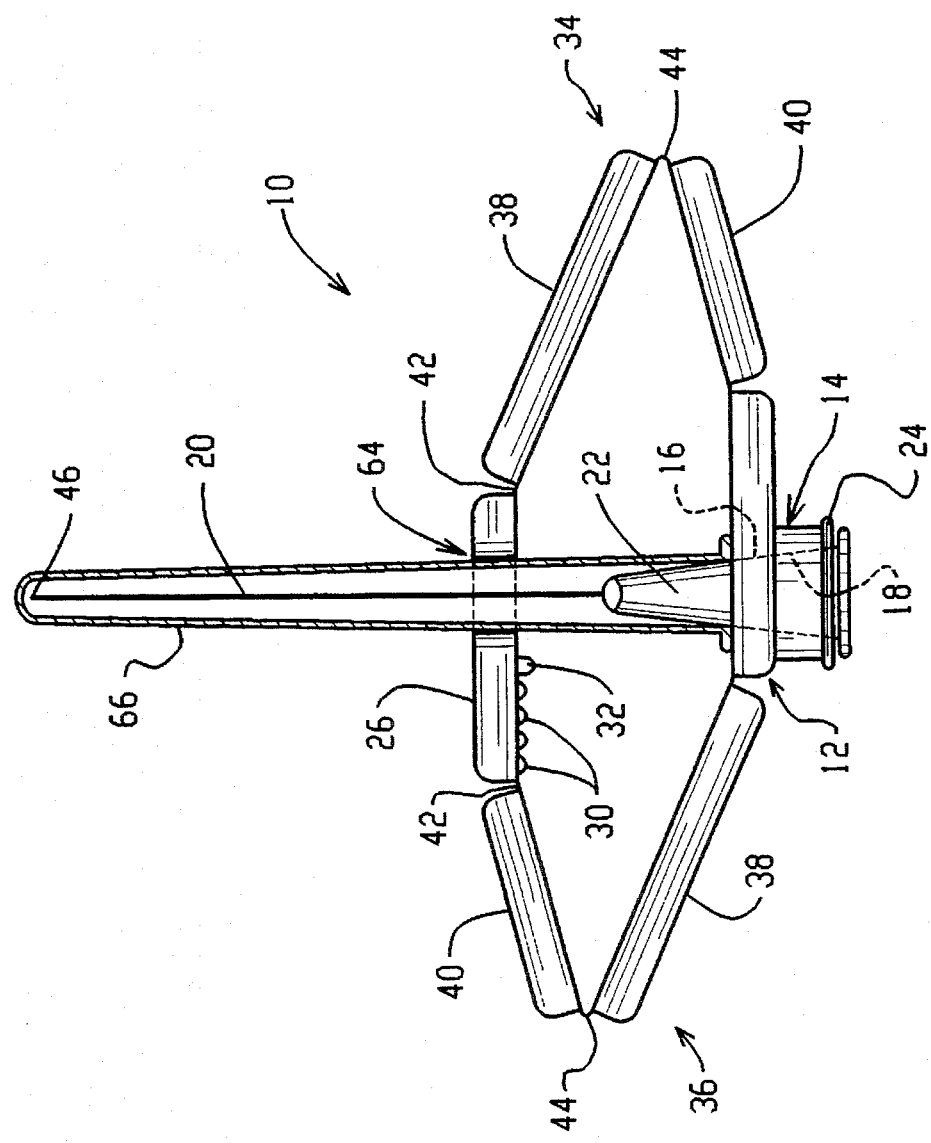

NEEDLE PUNCTURE PREVENTION DEVICE

BACKGROUND

Accidental needle puncture injuries are a major concern among health care workers worldwide. The risk of infection with hepatitis viruses, Acquired Immune Deficiency Syndrome (AIDS) virus and other blood-borne pathogens, due to inadvertent injury by contaminated needles, is genuine and well documented in the medical literature.

Many attempts have been made to design safety devices that minimize the risk of accidental needle sticks after needle use and during and after disposal. The safety devices fall into several categories. These include spring-loaded needle guards and needle sheaths which are manually or automatically activated to cover or blunt the needle tip after use; syringes with devices that retract the needle into the syringe after use; syringes with attached hinged needle enclosures which are manually rotated or pivoted into place to shield the needle and needle tip after use; and syringes fitted with outer barrel sheaths which manually or automatically slide up and lock over the needle tip after use.

However, there are many disadvantages associated with the afore-mentioned devices. Foremost among the disadvantages is that the devices have multiple components, require tight tolerances in fabrication, and are expensive to manufacture, thereby contributing to rising medical costs. Moreover, the sheathed syringes have added bulk which contributes to disposal problems. The complicated nature of spring-loaded needle guards and sheaths makes them more prone to failure during use and after disposal and they are more expensive than conventional needles and syringes. These devices are also limited in usage, as few can be adapted to fit a range of standard disposable hypodermic needles and syringes, vacuum-tube phlebotomy needles, intravenous catheters and winged steel needles.

Therefore, there is still a need for a simple, reliable, inexpensive and cost-effective needle safety device to prevent accidental needle puncture injuries.

SUMMARY

The present invention is directed to a simple, one-piece device designed to prevent needle puncture injuries after the needle is used and during disposal. The device comprises a base member connected to a top member by two substantially identical opposed sidewalls which are inverted with respect to each other. Each of the sidewalls comprises two sidewall members of unequal length which are connected to each other by sidewall living hinges. The base member, top member and the sidewalls are also interconnected by living hinges.

The base member comprises a first opening aligned with a second opening in a contiguous needle hub housing. The top member comprises a third opening which is positioned eccentrically on the longitudinal axis of the top member. When the device is in a relaxed condition, the sidewall living hinges are open, and the first and second openings in the base member are aligned with the third opening in the top member. A needle and needle hub may then be passed through the openings in the base member and the needle extended through the opening in the top member so that the needle is exposed for use. The needle hub is frictionally engaged by the needle hub housing of the base member and, if the needle is attached to a syringe, the needle hub housing is further threadably engaged to the syringe.

After use, the device is biased by the user into an extended condition, in which the needle is housed within the device. To accomplish this, the user manually biases the sidewall living hinges to a closed position by biasing the opposed sidewalls toward each other. The eccentric opening in the top member is now no longer aligned with the openings in the base member and the needle is extracted from the opening in the top member. Because the device has a reflexive tendency to try to be in the relaxed condition, the top member seats itself onto the needle tip and the needle tip is engaged by a needle tip engaging configuration, adjacent to the eccentric opening, on the bottom surface of the top member. Thus, the needle tip is securely housed within the device after use, and unintended needle punctures are prevented.

The needle puncture prevention device disclosed herein is inexpensive to manufacture, easy to use, and does not require specialized training of the user. The device is designed to be reliable and not become detached from the needle during or after disposal. Further, it is not bulky and does not add to disposal problems. It is envisioned that the device can be manufactured to adapt to any size or shape of needle and needle hub including, but not limited to, industry-standard hypodermic needles, intravenous catheter needles, vacuum-tube phlebotomy needles and winged steel needles. It is also envisioned that the device may be attached to the needle hub manually by the user before use, or may be integrated with a needle hub and/or a needle and syringe assembly at the point of manufacture.

These and other features, aspects, and advantages of the present invention will become better understood with regard to the following description, appended claims, and accompanying drawings.

BRIEF DESCRIPTION OF THE DRAWINGS

FIGS. 7A, 7B and 7C are front views of the lever means integral with the sidewall members.

FIGS. 8A and 8B are front views of the device in a relaxed condition, illustrating a groove in the top member for fitting a needle cap.

DETAILED DESCRIPTION

Figure 1:
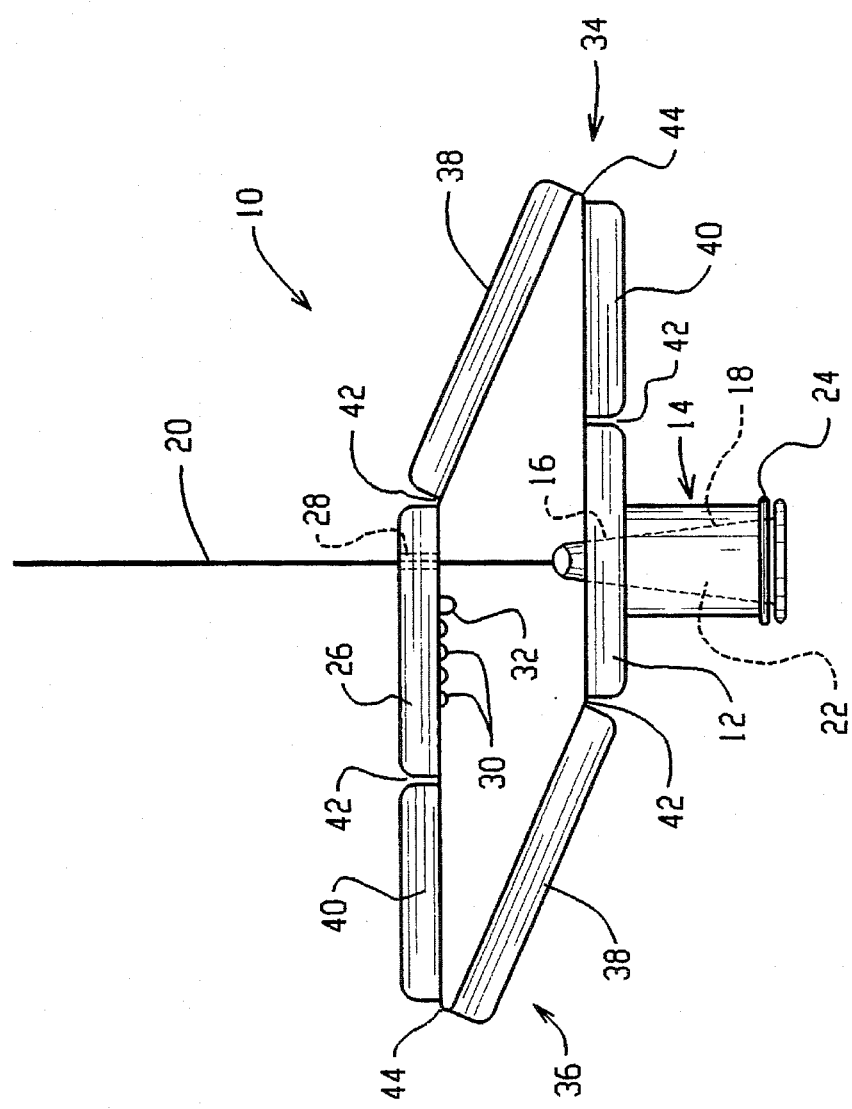
FIG. 1 is a front view of the device in a relaxed condition, attached to a hypothetical needle and needle hub.
Figure 3:
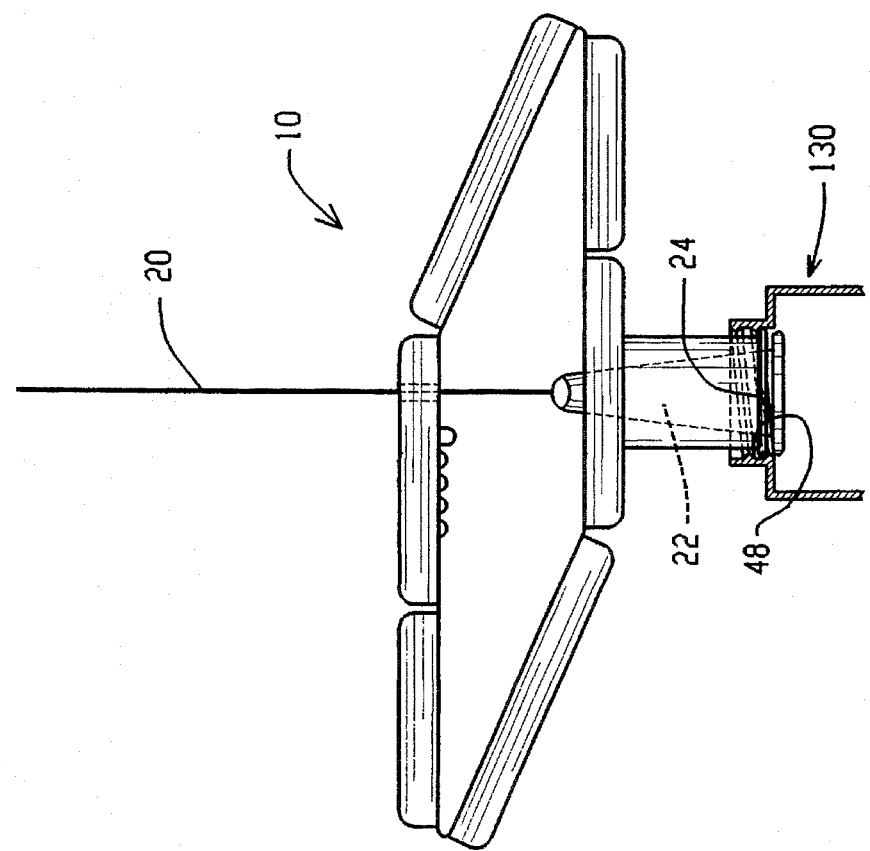
FIG. 3 is a front view of the device in a relaxed condition, as attached to a hypothetical needle and syringe assembly.

In general, the needle puncture prevention device of the present invention comprises a one-piece sleeve (10) shown in a relaxed condition in FIG. 1. The sleeve (10) comprises a base member (12) which, on its bottom surface, is contiguous with a needle hub housing (14). The base member has a first opening (16) therethrough which is aligned with a second opening (18) in the needle hub housing (14) to allow passage of a needle (20) and a needle hub (22). At least one of the openings (16) and (18) is shaped to frictionally engage the needle hub (22). The needle hub housing (14) may further comprise a lip (24) for threadably engaging the threads (48) of a syringe (130) attached to the needle (20) and needle hub (22), as shown in FIG. 3. The needle hub housing may be adapted to fit any size or shape of needle hub and any type of syringe.

The device of the present invention, as shown in FIG. 1, further comprises a top member (26) which has a bore (28) therethrough centrally positioned on the transverse axis and eccentrically positioned on the longitudinal axis of the top member (26), and sized to allow passage of the needle (20) therethrough. Adjacent to the bore (28), on the bottom surface of the top member there is a needle tip engaging configuration which, in this embodiment, is a plurality of parallel ribs (30) which run perpendicular to the longitudinal axis of top member (26). (See also FIG. 5A). The rib immediately adjacent to the bore (28) is of greater height with respect to the other ribs (30) and comprises a lip (32).

The sleeve (10) of FIG. 1 further comprises a pair of sidewalls (34) and (36) which are inverted with respect to each other and are connected to the base member (12) and to the top member (26) by means of living hinges (42). Each of the sidewalls (34) and (36) comprises a first sidewall member (38) and a second sidewall member (40) of unequal lengths which are also connected to each other by living hinges (44). When the device (10) is in the relaxed condition shown in FIG. 1, the base member (12) and the top member (26) are substantially parallel to each other, the first sidewall members (38) are substantially parallel to each other and the second sidewall members (40) are substantially parallel to each other. Thus, in the relaxed condition, the sidewall living hinges (44) are open and the device (10) substantially forms a parallelogram. In this condition, the eccentrically positioned bore (28) in the top member (26) is aligned with the first opening (16) in the base member (12) and the second opening (18) in the needle hub housing (14), thereby allowing the user to thread the needle and needle hub through the second opening (18) and the first opening (16) and to further thread the needle (20) through the bore (28). The user then slides the device (10) down to anchor it to the needle (20) and needle hub (22). The needle (20) is then free for use. If, as in FIG. 3, the needle hub (22) is attached to a syringe (130), the device (10) is then rotated and the lip (24) of the needle hub housing (14) threadably engages the syringe (130).

Figure 2:
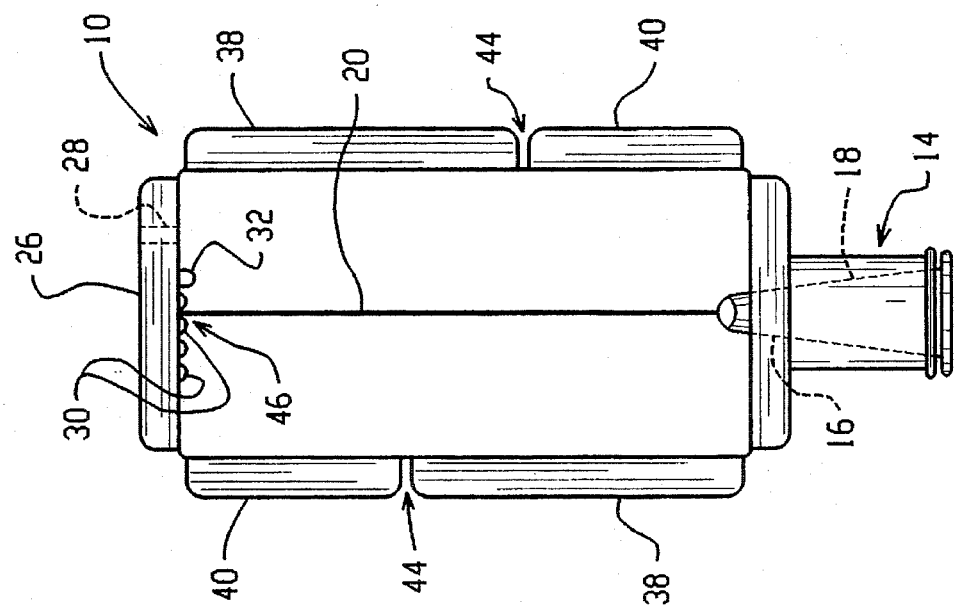
FIG. 2 is a front view of the device in an extended condition.

After the needle has been used, the sleeve (10) is raised to its extended position to protect the needle tip, as shown in FIG. 2. This is accomplished by the user manually biasing the sidewalls (34) and (36) toward each other by squeezing them between thumb and forefinger (not shown), thereby closing the sidewall living hinges (44). The sleeve (10) in the extended condition is substantially rectangular in shape in the embodiment of FIG. 2, and has an internal longitudinal dimension just sufficient for enclosing the tip (46) of the needle (20). When the sleeve (10) is extended by the user, the needle (20) is extracted from the eccentrically positioned bore (28) in the top member (26), and the bore (28) is no longer aligned with the first opening (16) in the base member (12) and the second opening (18) in the needle hub member (14). Because the sleeve has a reflexive tendency to try to be in the relaxed condition, the top member (26) seats itself onto the needle tip (46) and the needle tip (46) is engaged by the parallel ribs (30) on the bottom surface of the top member (26). The lip (32) and parallel ribs (30) prevent the needle tip (46) from reentering the eccentrically positioned bore (28). The needle tip (46) is now firmly capped inside the protective sleeve (10) and will remain there, thereby preventing accidental needle puncture injury to the user and to others during disposal.

Figure 4:
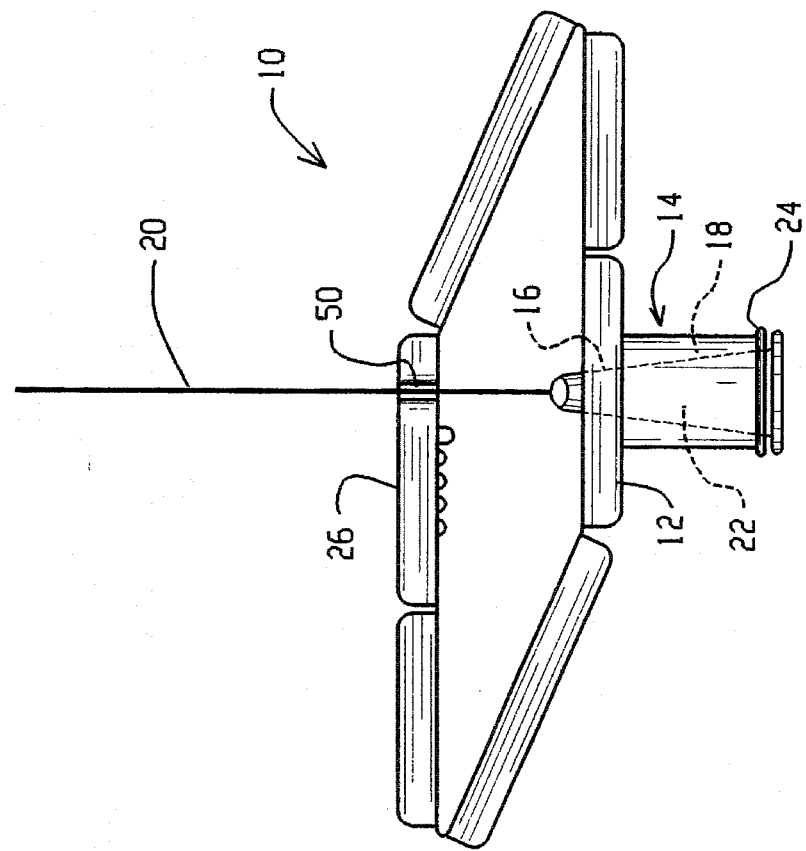
FIG. 4 is a front view of the device in a relaxed condition, illustrating a groove in the top member and a bore in the base member.
Figure 5A:
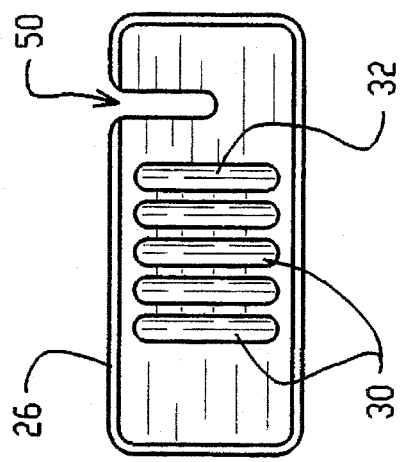
FIG. 5A illustrates the bottom surface of the top member.
Figure 5B:
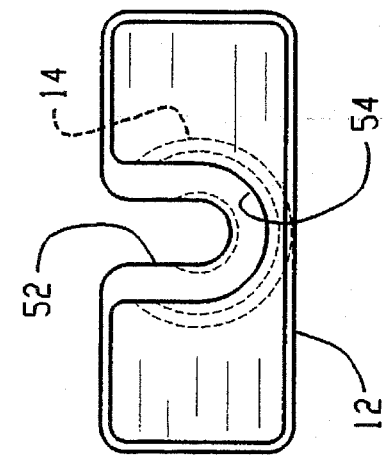
FIG. 5B illustrates a groove in the base member.
Figure 5:
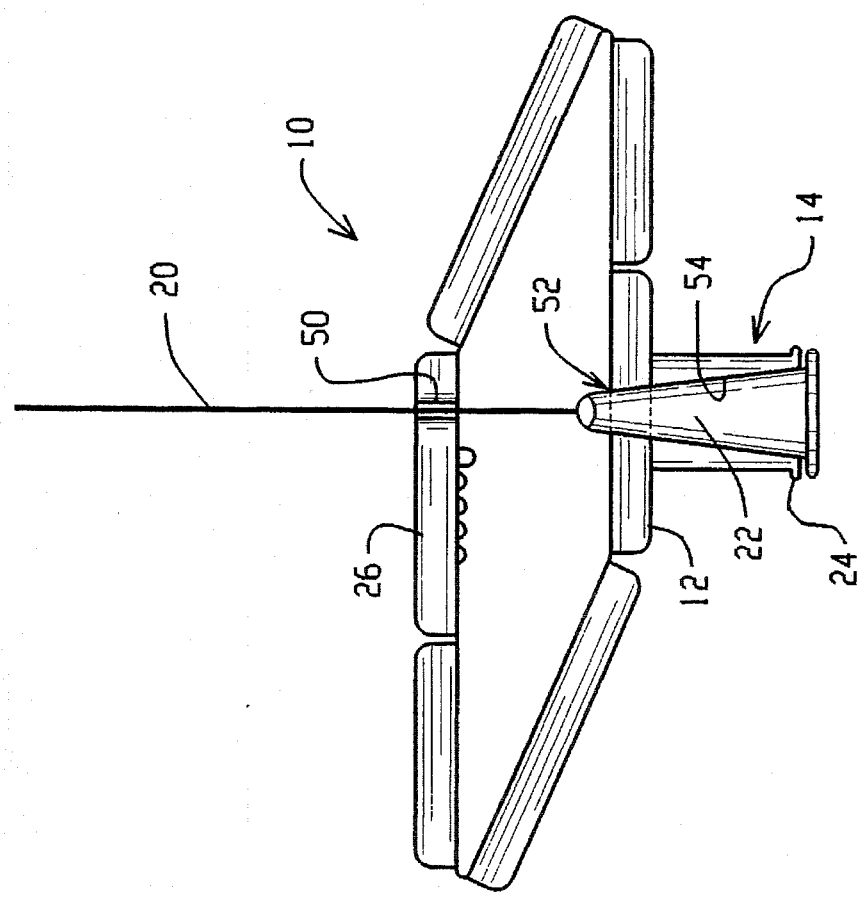
FIG. 5 is a front view of the device in a relaxed condition, illustrating a groove in the top member and a groove in the base member.
Figure 6:
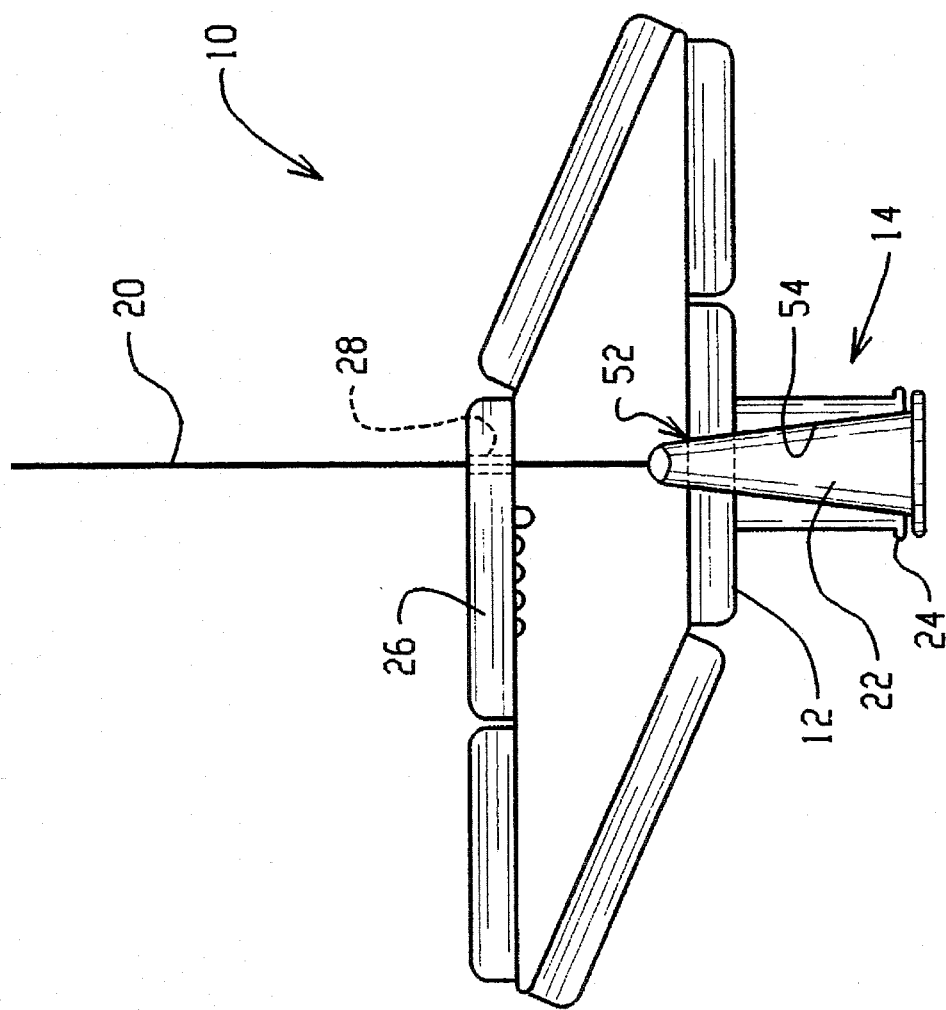
FIG. 6 is a front view of the device in a relaxed condition, illustrating a groove in the base member and an bore in the top member.

Alternative embodiments of the sleeve (10) are shown in FIGS. 4, 5, and 6. The sleeve (10) is shown in the relaxed position in these figures and the extended position, although not shown, corresponds to that of FIG. 2. In FIG. 4, rather than being a bore, the eccentrically positioned opening for the needle (20) in the top member (26) is a groove (50) for receiving the needle (20). To attach the sleeve (10) to the needle (20), the user threads the needle (20) and needle hub (22) through the second opening (18) in the needle hub housing (14) and the first opening (16) in the base member (12) and lays the needle down into the groove (50). The user then slides the sleeve (10) down to anchor it to the needle (20) and needle hub (22). If, as in FIG. 3, the needle hub (22) is attached to a syringe (130), the sleeve (10) is then rotated and the lip (24) of the needle hub housing (14) threadably engages the syringe (130).

The embodiment shown in FIGS. 5, 5A and 5B is similar to that of FIG. 4, in that the eccentric opening in the top member (26) is a groove (50) shaped to receive the needle (20). In this embodiment, the first opening in the base member (12) is a groove (52) aligned with a second groove (54) in the needle hub housing (14) and both grooves (52) and (54) are further aligned with groove (50) and at least one of grooves (52) and (54) is shaped to frictionally engage the needle hub (22). To attach the sleeve (10) to the needle (20), the user simply lays down the needle and needle hub into the grooves, then slides the sleeve (10) down to engage the needle hub (22). If, as in FIG. 3, the needle hub (22) is attached to a syringe (130), the sleeve (10) is then rotated and the lip (24) of the needle hub housing (14) threadably engages the syringe (130).

In the embodiment shown in FIG. 6, the opening in the top member (26) of the sleeve (10) is the eccentrically positioned bore (28) as shown in FIG. 1, for allowing passage of the needle (20). The grooves (52) and (54) in the base member (12) and needle hub housing (14), for frictionally engaging the needle hub (22), are as shown in FIGS. 5 and 5B. In this embodiment, to attach the sleeve (10) to the needle (20), the user threads the needle (20) through the bore (28), lays the needle hub (22) down into the grooves (52) and (54), and then slides the sleeve (10) down to engage the needle hub (22). If, as in FIG. 3, the needle hub (22) is attached to a syringe (130), the sleeve (10) is then rotated and the lip (24) of the needle hub housing (14) threadably engages the syringe (130).

In the embodiment presented in FIGS. 7A, 7B and 7C, the device has finger tabs (60) extending outwardly from the sidewall members (38). The finger tabs could alternatively be extensions of sidewall members (40) and/or (38). The finger tabs (60) may be integral extensions of the sidewall members (38) and/or (40) or, alternatively, may be attached separately and may also be removable. To enclose the needle (20) and needle tip (46) in the sleeve (10), the user manually squeezes the outwardly extending finger tabs (60) toward each other and thereby biases the sidewall living hinges into a closed position. The needle tip (46) is engaged by the ribs (30) and (32) and the finger tabs (60) now extend inwardly to the sleeve. The shape of the figure tabs (60) is not limited to the embodiment shown in FIGS. 7A, 7B and 7C, but can be any shape which will provide the leverage means to bias the sidewall hinges (44) into the closed position. The finger tabs (60) may also be provided with a friction means (62), to allow a better grip by the user.

An embodiment shown in FIG. 8A is modified in several respects from that shown in the previous figures. In this embodiment, the needle hub housing (14) has been shortened. This shortening allows the needle hub housing (14) to ride lower on the needle hub (22), allowing for more of the needle (20) to be exposed for use. The walls of the needle hub housing (14) also have been thickened to allow for more strength when the lip (24) is threaded into the syringe (shown in FIG. 3). In this embodiment, the needle hub housing (14) is eccentrically positioned on the longitudinal axis of the base member (12). The opening (16) in the base member (12) and the opening (18) in the needle hub housing (14) may be a bore (18) as shown in FIGS. 1–4, or a groove, as shown in FIGS. 5 and 6. The opening (64) in the top member (26) may be a bore as shown in FIGS. 1–3 and 6, or a groove, as shown in FIGS. 4 and 5. In this embodiment, the shape of the sleeve (10) in the relaxed condition is a trapezoid, rather then a parallelogram, in order that the alignment of the openings (16) and (18) in the base member (12), the needle hub housing (14) and the eccentrically positioned opening (64) in the top member (26) is preserved. As shown in FIG. 8A, the eccentrically positioned opening in top member (26) of the sleeve (10) is a groove (64), shown further in FIG. 8B, which is sized to receive a needle cap (66) placed over the needle (20). This modification allows the user, after attaching the device (10) to a needle and syringe assembly (see FIG. 3), to fill the syringe (130) with reagent before use and then recap the needle (20) before transport to the treatment area. The needle is then uncapped, the treatment administered, and the sleeve (10) biased manually into the extended condition by the user, as before, by closing the sidewall living hinges (44). The needle tip (46) is then engaged by the ribs (30) adjacent to the groove (64) and prevented from reentering the groove (64) by the raised rib (32).

Figure 9B:
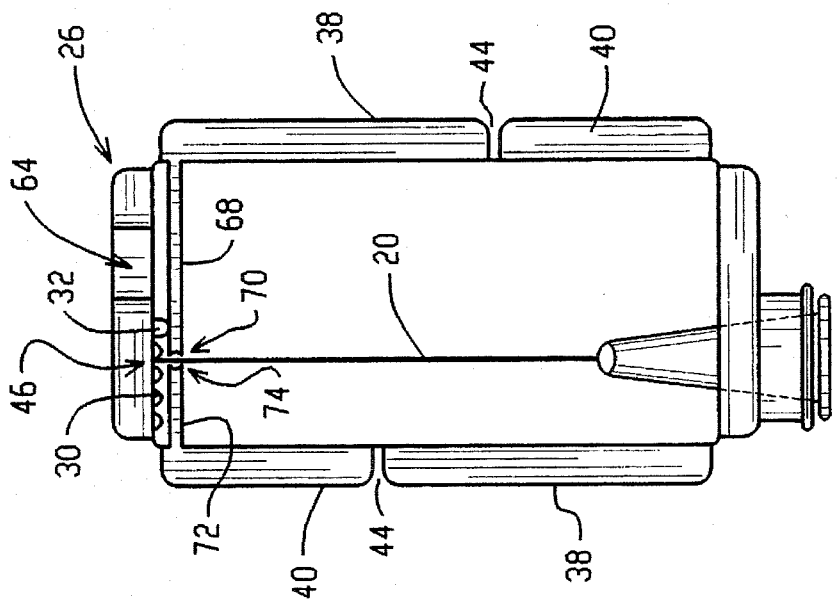
FIG. 9B is a front view of the device in an extended condition, illustrating the needle trapping means.
Figure 9A:
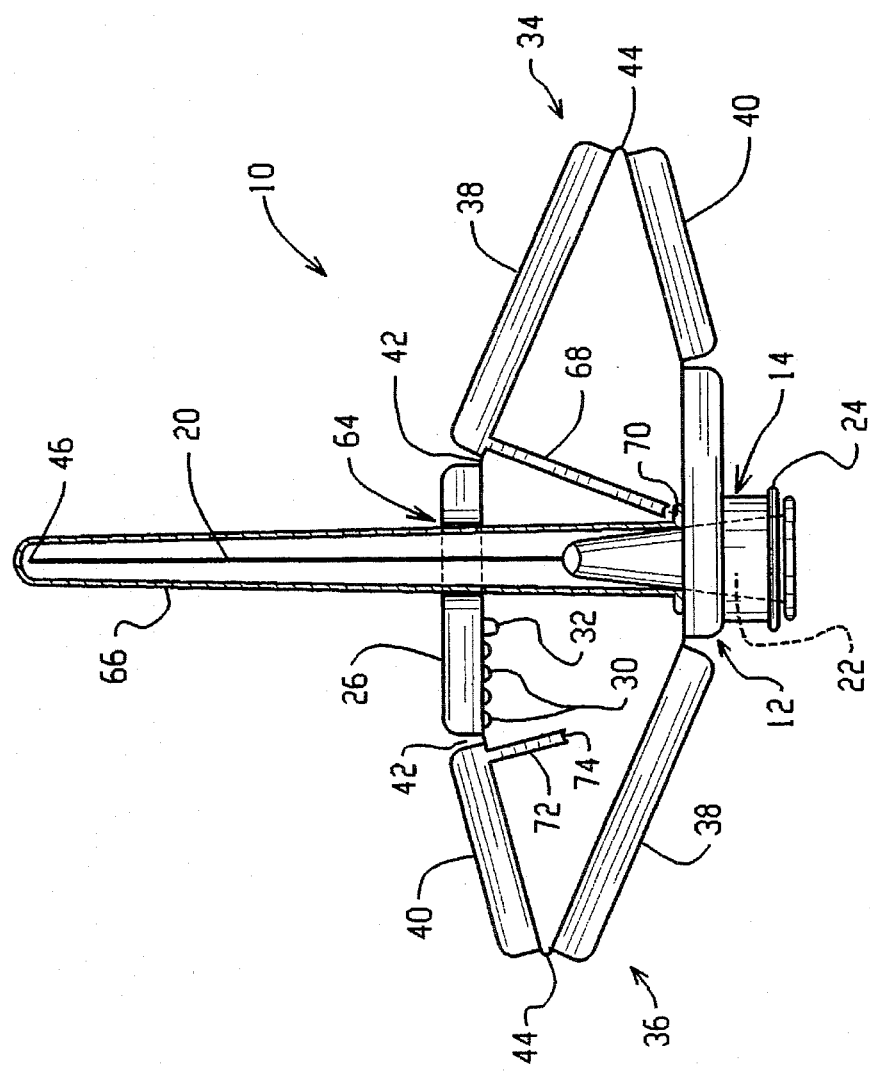
FIG. 9A is a front view of the device in a relaxed condition, illustrating a needle trapping means.

Another embodiment of the device is illustrated in FIGS. 9A and 9B. In this embodiment, needle trapping arms (68) and (72) are provided in addition to the needle tip engaging configuration (30) and (32) shown in the previous figures. Although the embodiment is illustrated with the needle (20) enclosed in the needle cap (66) contained in the groove (64), the needle trapping arms (68) and (72) may be used with any of the illustrated embodiments of the device. As shown in FIG. 9A, the needle trapping arms (68) and (72) are integral with sidewall members (38) and (40), and extend downwardly and substantially perpendicularly therefrom. It is not essential that the arms extend perpendicularly, but any angle between the arms and the sidewall members that achieves the purpose of the arms is acceptable. Each of the arms (68) and (72) is positioned substantially adjacent to and biased toward the bottom surface of the top member (26). The arm (68) is of greater length than the arm (72). Each of the arms (68) and (72) has an end comprising a needle trapping means (70) and (74) which, in this embodiment comprises complementary notches. However, any means which will serve this purpose is acceptable. When the sleeve (10) is in the relaxed condition, the arms (68) and (72) are biased toward each other forming an opening to allow passage of the needle (20) and/or the needle (20) with needle cap (66) therebetween. When the sleeve (10) is in the extended condition, the needle (20) is housed within the sleeve (10), the needle tip (46) is engaged by the ribs (30) and (32), the arms (68) and (72) are further biased toward each other and the bottom surface of the top member (26). The arm (68) is sufficient in length to shield the opening (64) in the top member (26) and the needle trapping means (70) and (74) trap the needle (20) and prevent the needle tip (46) from moving off of the ribs (30) and (32). This embodiment particularly assures that the sleeve (10) will not become disengaged from the needle tip (46) during and after disposal.

Figure 10A:
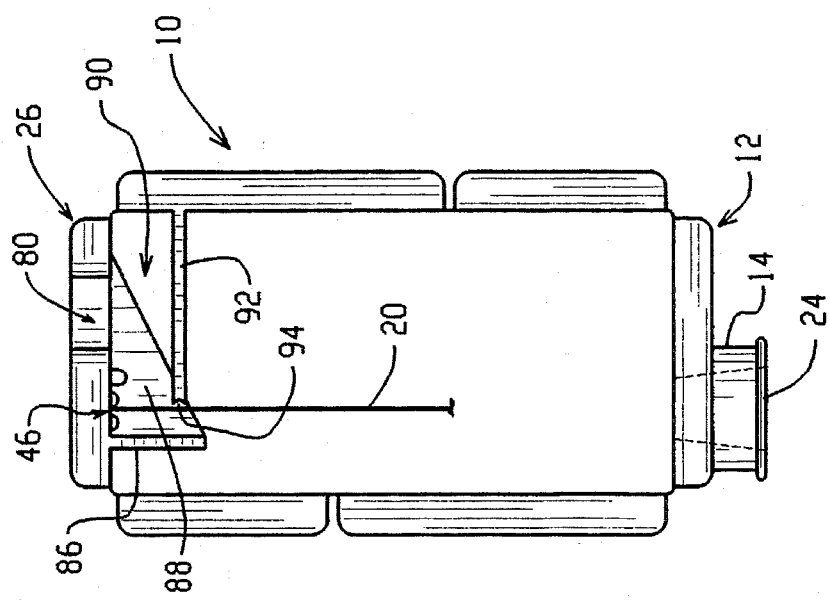
FIG. 10A is a front view of the device in a relaxed condition, illustrating a needle trapping box.
Figure 10B:
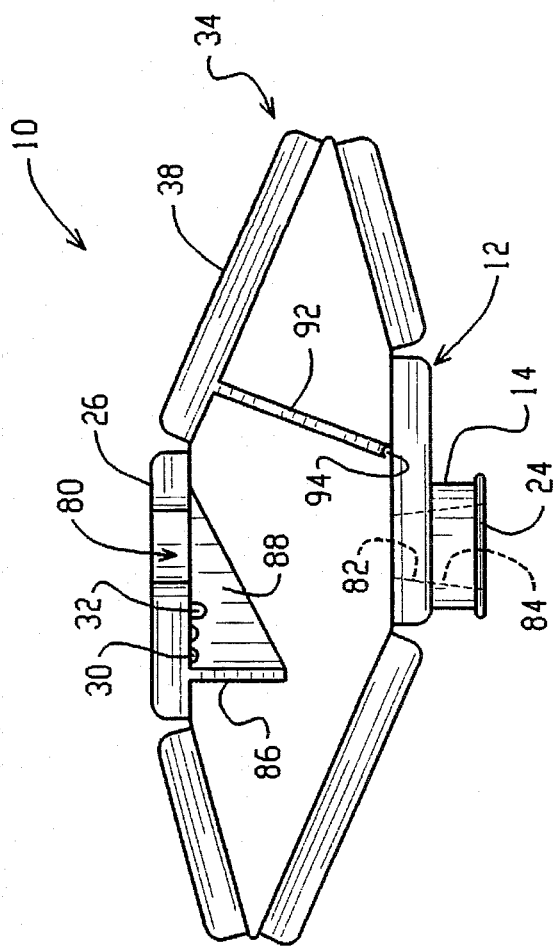
FIG. 10B is a front view of the device in an extended condition, illustrating the needle trapping box.
Figure 10C:
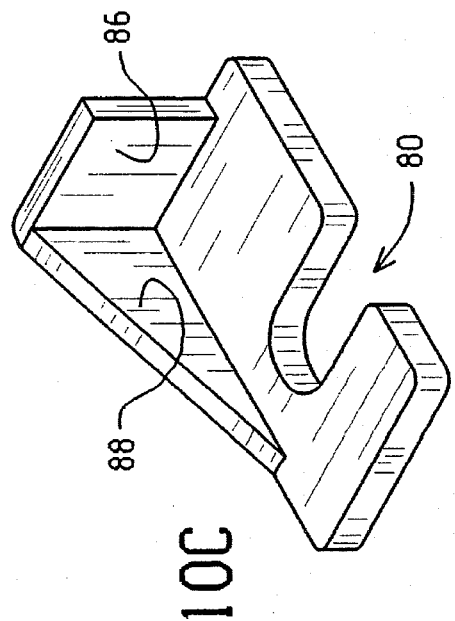
FIG. 10C is an oblique view of the three-sided needle trapping box.

Another embodiment of the device is illustrated in FIGS. 10A, 10B and 10C. This embodiment is similar to that illustrated in FIG. 8A. As in FIG. 8A, the needle hub housing (14) has been shortened to allow the needle hub housing (14) to ride lower on the needle hub, allowing for more of the needle to be exposed for use. The walls of the needle hub housing (14) are thick to provide strength when the lip (24) is threaded into the syringe (130) (shown in FIG. 3). The needle hub housing (14) is eccentrically positioned on the longitudinal axis of the base member (12). The opening (82) in the base member (12) and the opening (84) in the needle hub housing (14) may be a bore as shown in FIGS. 1–4 and 8–9 or a groove, as shown in FIGS. 5 and 6. In this embodiment, the shape of the sleeve (10) in the relaxed condition is a trapezoid, rather then a parallelogram, in order that the alignment of the openings (82) and (84) and the eccentrically positioned opening (80) in the top member (26) is preserved. The opening (80) in top member (26) of the sleeve (10) may be a bore, as illustrated in FIGS. 1–3 and 6 or a groove, as illustrated in FIGS. 4, 5, 8A, 8B, 9A and 9B.

In the embodiment illustrated in FIGS. 10A, 10B and 10C, the top member (26) further comprises a first wall (86) which is contiguous with the bottom surface of the top member (26) and which extends substantially perpendicularly therefrom. The first wall (86) is positioned proximal to and substantially parallel to the needle tip engaging ribs (30) and (32) and is distal to the opening (80) in the top member (26). The top member (26) further comprises a second wall (88) which is contiguous with the bottom surface of the top member (26) and extends substantially perpendicularly therefrom. The second wall (88) is positioned adjacent to and substantially perpendicular to the needle tip engaging ribs (30) and (32) and is distal to the opening (80). The first and second walls (86) and (88) are contiguous with each other and form substantially a 90° angle with each other. Together with the bottom surface of the top member (26), the first and second walls (86) and (88) substantially form three sides of a needle trapping box (90), shown in FIG. 10B. The needle trapping box (90) further comprises an arm (92) integral with a first or second sidewall member (38) adjacent to and hinged to an end of the top member (26) proximal to the opening (80). The arm (92), which has an end comprising a needle trapping means (94), such as a notch, extends downwardly from the sidewall member (38) and is positioned substantially adjacent to and is biased toward the bottom surface of the top member (26) and the three-sided needle trapping box (90). When the sleeve (10) is in the relaxed condition, the arm (92) is biased toward the three-sided needle trapping box (90), forming an opening to allow passage of the needle (20) and/or the needle (20) and needle cap (66) (not shown) therebetween, and through the opening (80). When the sleeve is in the extended condition, the needle (20) is housed within the sleeve (10), the needle tip (46) is engaged by the ribs (30) and (32), the arm (92) is further biased toward the three-sided needle trapping box (90) to form substantially a fourth side of the box to trap the needle therebetween.

In all of the illustrated embodiments, the members of the sleeve are shown to be "plank-shaped"; however, any shape of the members that serves the purpose of the invention is acceptable. The device may be injection molded and made from a thermoplastic material, such as polypropylene. However, it is envisioned that the device could be made from any material, including metals.

Although the present invention has been described in considerable detail with reference to certain preferred embodiments thereof, it is not intended to limit the scope of the invention to particular embodiments set forth but, to the contrary, it is intended to cover such alternatives, modifications, and equivalents as may be included within the spirit and scope of the invention as defined by the appended claims.

I claim:

1. A needle puncture prevention device, comprising:
   a) a base member having a top surface and a bottom surface and a first opening therethrough, said bottom surface being contiguous with a needle hub housing having a second opening aligned with said first opening for allowing passage therethrough of a needle comprising a needle tip and a needle hub, at least one of said first and second openings being shaped to frictionally engage said needle hub;
   b) a top member having a longitudinal axis, said top member further having a top surface and a bottom surface and a third opening therethrough for allowing passage of a needle therethrough, said third opening positioned eccentrically on said longitudinal axis, said bottom surface of said top member being opposed to said top surface of said base member, said bottom surface having a needle tip engaging configuration;
   c) a primary sidewall comprising a first sidewall member having a first longitudinal dimension and a second sidewall member having a second longitudinal dimension, said first and second longitudinal dimensions being unequal in length and said first and second sidewall members being connected to each other by a primary sidewall living hinge, said first sidewall member further being connected to said base member by a living hinge, and said second sidewall member further being connected to said top member by a living hinge; and
   d) a secondary sidewall comprising a first sidewall member and a second sidewall member, said first sidewall member having the same length dimension as said primary first sidewall member, said first and second sidewall members being connected to each other by a secondary sidewall living hinge, said first sidewall member further being connected to said top member by a living hinge, and said second sidewall member further being connected to said base member by a living hinge;
   wherein when said device is in a relaxed condition, said primary and secondary sidewall hinges are open, and said third opening in said top member is aligned with said first and second openings of said base member to allow extension of a needle therethrough; and wherein, when said device is in an extended condition, said primary and secondary sidewall hinges are closed, the needle is housed within said device, said third opening in said top member is eccentric to the needle tip, and the needle tip is secured by said needle tip engaging configuration of said top member to prevent the needle from reentering said third opening, thereby preventing unintended needle punctures.

2. The device recited in claim 1, wherein a primary sidewall member and a secondary sidewall member further comprise a lever means integral with said members and extending longitudinally therefrom at said primary and secondary sidewall living hinges, said lever means extending outwardly from said device when said device is in a relaxed condition and inwardly to said device when said device is in an extended condition.

3. The device recited in claim 2, wherein said lever means comprises a finger tab.

4. The device recited in claim 3, wherein said lever means further comprises a friction means.

5. The device recited in claim 1, wherein said needle tip engaging configuration comprises a plurality of parallel ribs perpendicular to said longitudinal axis of said top member and positioned centrally thereon, said ribs positioned adjacent to said third opening, and wherein a rib immediately adjacent to said third opening comprises a lip.

6. The device recited in claim 1, wherein said top member further comprises a first wall contiguous with said bottom surface of said top member and extending substantially perpendicularly therefrom, said first wall being adjacent to said sidewall furthest from said third opening; and said top member further comprises a second wall contiguous with said bottom surface of said top member and extending substantially perpendicularly therefrom, said second wall positioned adjacent to said sidewall furthest from said third opening, said second wall being contiguous with and forming substantially a 90° angle with said first wall, whereby said first wall, said second wall and said bottom surface substantially form three sides of a box with said needle tip engaging configuration contained therein for trapping a needle; and wherein the sidewall member adjacent to said top member and closest to said third opening further comprises an arm, said arm being integral with said sidewall member and extending downwardly therefrom, said arm being positioned substantially adjacent to and biased toward said bottom surface of said top member and said three-sided box, and said arm further having an end comprising a needle trapping means; and wherein when said device is in a relaxed condition, said arm is biased away said three-sided box, forming an opening to allow passage of a needle therebetween and through said third opening in said top member; and wherein, when said device is in an extended condition and the needle is housed within said device and the needle tip is engaged by the needle tip engaging configuration, said arm is further biased toward said threesided box to form substantially a fourth side of said box and to trap the needle therebetween.

7. The device recited in claim 6, wherein said needle trapping means comprises a notch in said end of said arm.

8. The device recited in claim 6, wherein when said device is in a relaxed condition, said arm and said three-sided box form an opening to allow passage of a needle and needle cap therebetween.

9. The device recited in claim 1, wherein a primary sidewall member adjacent to said top member and a secondary sidewall member adjacent to said top member each further comprises an arm integral with said member and extending downwardly and substantially perpendicularly therefrom, each of said arms positioned substantially adjacent to and biased toward said bottom surface of said top member, each of said arms further having an end comprising a needle trapping means; and wherein when said device is in a relaxed condition, said arms are biased toward each other forming an opening to allow passage of the needle therebetween; and wherein, when said device is in an extended condition and the needle is housed within said device, said arms are further biased toward said bottom surface of said top member and one of said arms shields said third opening therein, and each of said ends of said arms are further biased toward each other to secure the needle therebetween by said needle trapping means.

10. The device recited in claim 9, wherein when said device is in the relaxed condition, said arms are biased toward each other forming an opening to allow passage of a needle and a needle cap therebetween.

11. The device recited in claim 9, wherein said needle trapping means comprises a complementary notch in each of said ends of said arms.

12. The device recited in claim 1, wherein said device is formed from a thermoplastic material.

13. The device recited in claim 12, wherein said material comprises polypropylene.

14. The device recited in claim 1, wherein said base member further comprises a longitudinal axis and said first opening and said needle hub housing are positioned centrally on said longitudinal axis.

15. The device recited in claim 1, wherein said base member further comprises a longitudinal axis and said first opening and said needle hub housing are positioned eccentrically on said longitudinal axis.

16. The device recited in claim 14 or claim 15, wherein said first opening, said second opening and said third opening are of the same kind and are selected from the group consisting of a bore and a groove.

17. The device recited in claim 14 or claim 15, wherein said first opening, said second opening and said third opening are selected from the group consisting of a bore and a groove.

18. The device recited in claim 1, wherein said needle hub housing further comprises means for threadably engaging a syringe attached to the needle hub.

19. The device recited in claim 1, wherein the needle further comprises a needle cap and said third opening in said top member further allows passage of said needle cap therethrough.

20. The device recited in claim 1, wherein said device in said relaxed condition is substantially a parallelogram, and in said extended condition is substantially a rectangle.

21. The device recited in claim 1, wherein said device in said relaxed condition is substantially a trapezoid, and in said extended condition is substantially a rectangle.

22. The device recited in claim 1, wherein said device is formed in one piece.

* * * * *